(12) United States Patent
Swenson et al.

(10) Patent No.: US 6,808,928 B1
(45) Date of Patent: Oct. 26, 2004

(54) DESORPTIVE METHOD FOR DETERMINING A SURFACE PROPERTY OF A SOLID

(75) Inventors: LaSalle R. Swenson, Chicago, IL (US); Timothy A. Brandvold, Arlington Heights, IL (US); Michael J. McCall, Geneva, IL (US); Kurt M. Vanden Bussche, Lake in the Hills, IL (US); Richard R. Willis, Cary, IL (US)

(73) Assignee: UOP LLC, Des Plaines, IL (US)

( * ) Notice: Subject to any disclaimer, the term of this patent is extended or adjusted under 35 U.S.C. 154(b) by 331 days.

(21) Appl. No.: 10/076,797

(22) Filed: Nov. 7, 2001

Related U.S. Application Data

(63) Continuation-in-part of application No. 09/844,421, filed on Apr. 27, 2001.

(51) Int. Cl.$^7$ .......................... G01N 31/00; G01N 25/20
(52) U.S. Cl. .......................... 436/5; 436/167; 436/168; 436/147; 73/38
(58) Field of Search .......................... 436/5, 164, 167, 436/147; 73/38

(56) References Cited

U.S. PATENT DOCUMENTS

| | | | |
|---|---|---|---|
| 2,826,908 A | 3/1958 | Skarstrom | 73/23 |
| 3,850,040 A | 11/1974 | Orr, Jr. et al. | 73/432 |
| 4,237,200 A | * 12/1980 | Weddigen | 429/102 |
| 4,496,249 A | * 1/1985 | Lee et al. | 374/7 |
| 4,566,326 A | 1/1986 | Lowell | 436/5 |
| 5,360,743 A | 11/1994 | Lowell | 436/5 |
| 5,408,864 A | * 4/1995 | Wenman | 73/38 |
| 5,744,699 A | * 4/1998 | Suzuki | 73/38 |
| 6,063,633 A | 5/2000 | Wilson, III | 436/37 |

FOREIGN PATENT DOCUMENTS

| | | | | |
|---|---|---|---|---|
| WO | WO 98/15813 | 4/1998 | | G01N/21/35 |
| WO | WO 99/34206 | 7/1999 | | G01N/31/10 |
| WO | WO 00/36399 | 6/2000 | | B01N/21/25 |

OTHER PUBLICATIONS

Holzwarth, A.; Schmidt, H.; Maier, W.F. Angew, Chem Int. Ed. 1998, 37, No. 19, 2644, 2647.

Jandeleit, B.; Schaefer, D.J.; Powers, T.S.; Turner, H.W.; Weinberg, W.H. Angew. Chem. Int. Ed. 1999, 38, 2494–2532.

Marengo, S.; Raimondini, G.; Comotti, P. New Frontiers in Catalysis, Gucci, L. et al. Eds.; Proceedings in the $10^{th}$ International Congress on Catalysis, Jul. 19–24, 1992, Budapest, Hungary Elservier Science 1993 2574–2576.

Palkhiwala, A.G., Gorte, R.J. Catal Lett. 57, No. 1,2 (1998) p. 19–23.

Moates, F.C.; Somani, M.; Annamalai, J.; Richardson, J.T.; Luss, D.; Wilson, R.C. Ind. Eng. Chem. Res., 1996, 35, 4801–4803.

Pawlicki, P.C.; Schmitz, R.A. Chemical Engineering Progress, 1987, p. 40–45.

* cited by examiner

Primary Examiner—Jill Warden
Assistant Examiner—LaToya Cross
(74) Attorney, Agent, or Firm—John G. Tolomei; Frank S. Molinaro; Maryann Maas

(57) ABSTRACT

A method of determining a surface property of a plurality of solids by contacting the solids with a fluid, measuring the radiation emitted, absorbed, or altered during desorption of the fluid using a detector, and then determining at least one surface property of the solids from the radiation measurements has been invented. The invention is particularly useful in combinatorial applications in order to evaluate a plurality of solids or mixtures of solids to determine at least one surface property of each of the solids.

3 Claims, 12 Drawing Sheets

DESORPTIVE METHOD FOR DETERMINING A SURFACE PROPERTY OF A SOLID

CROSS REFERENCE TO RELATED APPLICATION

This application is a continuation in part application of our copending application Ser. No. 09/844,421 filed Apr. 27, 2001 which is hereby incorporated by reference in its entirety.

STATEMENT REGARDING FEDERALLY SPONSORED RESEARCH OR DEVELOPMENT

This invention was made under the support of the United States Government, Department of Commerce, National Institute of Standards and Technology (NIST), Advanced Technology Program, Cooperative Agreement Number 70NANB9H3035. The United States Government has certain rights in the invention.

FIELD OF THE INVENTION

The present invention relates to the general field of determining a surface property of one or more solids. More specifically, the present invention relates to monitoring the effect of desorption on the emission, absorption, or alteration of radiation by the material to determine the surface property.

BACKGROUND OF THE INVENTION

Many methods have historically been used to evaluate solids and determine their characteristics. For example, U.S. Pat. No. 5,408,864 B1 teaches a method of analyzing the characteristics of an adsorbent using a sample chamber of known volume and known temperature. An adsorptive gas is introduced and the pressure is measured. The quantity of gas adsorbed by the adsorbent at the measured pressure is determined. A relative pressure in the sample chamber and the quantity of adsorptive gas adsorbed by the adsorbent at the relative pressure is correlated. This method is a super atmospheric sub-critical temperature method for determining the amount of a gas adsorbed or desorbed by a solid in a manner such that the corresponding adsorption and desorption isotherms can be constructed. Characteristics such as surface area, pore size distribution, and pore volume can then be determined. Also, thermal effects of a compound being adsorbed on an adsorbent have been used in U.S. Pat. No. 2,826,908 B1 to help identify compounds present in a gas stream.

U.S. Pat. No. 4,566,326 B1 teaches an automatic adsorption and desorption analyzer for independently performing analyses on a plurality of powder samples. A manifold is connected through a plurality of independently operated valves to a corresponding plurality of sample cells. A pressure transducer measures the manifold pressure and a plurality of pressure transducers are respectively coupled to the sample cells to independently measure the pressure at each of the sample cells. The system measures the volume of gas adsorbed or desorbed by each of the samples that is required to establish specified equilibrium pressures at the sample cells to thereby provide pressure-volume points which can be used to prepare adsorption or desorption isotherms or BET curves. U.S. Pat. No. 5,360,743 B1 improves the teachings above by accounting for the void volume, the adsorption of the sample cell walls, and correcting for non-ideal gas behavior.

WO 99/34206 teaches a method for combinatorial material development where the reaction heat generated by chemical or physical processes in materials of combinatorial libraries are made visible by means of differential thermal images of an infrared camera.

U.S. Pat. No. 3,850,040 B1 teaches a gaseous sorption analysis apparatus and method for the measurement at cryogenic temperatures of factors such as surface area, adsorption isotherms and desorption isotherms. The system determines the dead space within a sample container and then adds to the evacuated container in an initial dose of an operating gas such as nitrogen which is equal to the known dead space and other constant volumetric factors plus an additional increment of gas corresponding to a first estimated amount of gas to be adsorbed by the sample. The amount of gas actually adsorbed by the sample is determined and this amount is used to determine the incremental amount of gas to be included in a second dose of gas supplied to the sample for adsorption. Subsequent doses of gas are applied to the sample as required to bring the total amount of gas adsorption up to a level which is a predetermined fraction of the gas saturation pressure of the sample at a fixed temperature. The foregoing steps are repeated a plurality of times to obtain a corresponding plurality of fixed points from which the BET curve is determined for a particular sample.

Infrared thermography has been used to detect and measure catalytic activity in combinatorial libraries of materials. See Holzwarth, A.; Schmidt, H.; Maier, W. F. Angew. Chem. Int. Ed. 1998, 37, No. 19, 2644–2647. U.S. Pat. No. 6,063,633 B1 teaches a method of simultaneously testing a plurality of catalyst formulations to determine comparative catalytic activity of the formulations in the presence of a given reactant or reactant mixture. The method involves supporting the plurality of catalyst formulations on a support and fixing the formulations on the support. The formulations are contacted with a common stream of the reactant or reactant mixture under reaction conditions. Comparative catalytic activity is detected at each of the formulations through sensing radiation admitted, adsorbed or altered by the respective formulations, reactant or products indicative of catalyst activity using a detector. Infrared spectroscopy and imaging of libraries has also been used in WO 98/15813 to determine thermodynamic characterization relating to the absorbable bulk properties of a material such as volume, enthalpy, heat capacity, free energy, heat of reaction, catalytic activity and thermal conductivity. Jandeleit, B.; Schaefer, D. J.; Powers, T. S.; Turner, H. W.; Weinberg, W. H. Angew. Chem. Int. Ed. 1999, 38, 2494–2532, teaches using infrared thermography to monitor temperature changes that arise from the exothermic catalytic acylation of ethanol.

Marengo, S.; Raimondini, G.; Comotti, P. New Frontiers in Catalysis, Gucci, L. et al Eds.; Proceedings of the 10th International Congress on Catalysis, 19–24 Jul., 1992, Budapest, Hungary Elservier Science 1993 2574–2576 teaches the evaluation of the adsorption properties of catalysts using infrared thermography and comparing thermal effects. The present invention, however, allows surface properties of solids to be determined through monitoring the changes in radiation emitted, absorbed, or altered by the solids upon adsorption or desorption of an adsorbate.

SUMMARY OF THE INVENTION

One purpose of the present invention is to provide a method of determining a surface property of each of a plurality of solids by contacting the solids with a fluid, measuring the radiation emitted, absorbed, or altered by the solids during contact with the fluid using a detector, and then determining at least one surface property of the solids from the radiation measurements. The invention is particularly useful in combinatorial applications in order to evaluate a plurality of solids or mixtures of solids to determine at least one surface property of each of the solids.

Another purpose of the invention is to provide a method of determining a surface property of at least one solid during desorption of an adsorbate. In this specific embodiment of the invention, the method involves supporting the plurality of solids on at least one support and contacting the plurality of solids with a fluid for a period of time. The fluid is discontinued, and adsorbed fluid is then desorbed from the plurality of solids while the radiation emitted, absorbed, or altered by the respective solids or mixture of solids is measured using a detector. The desorption may be accomplished by, for example, ramping the temperature or the pressure within the apparatus. This specific embodiment may be applied to a single solid as well as to a plurality of solids.

Another purpose of the invention is a method to quantify the amount of a material adsorbed or desorbed by one or more solids.

DETAILED DESCRIPTION OF THE INVENTION

Figure 1:
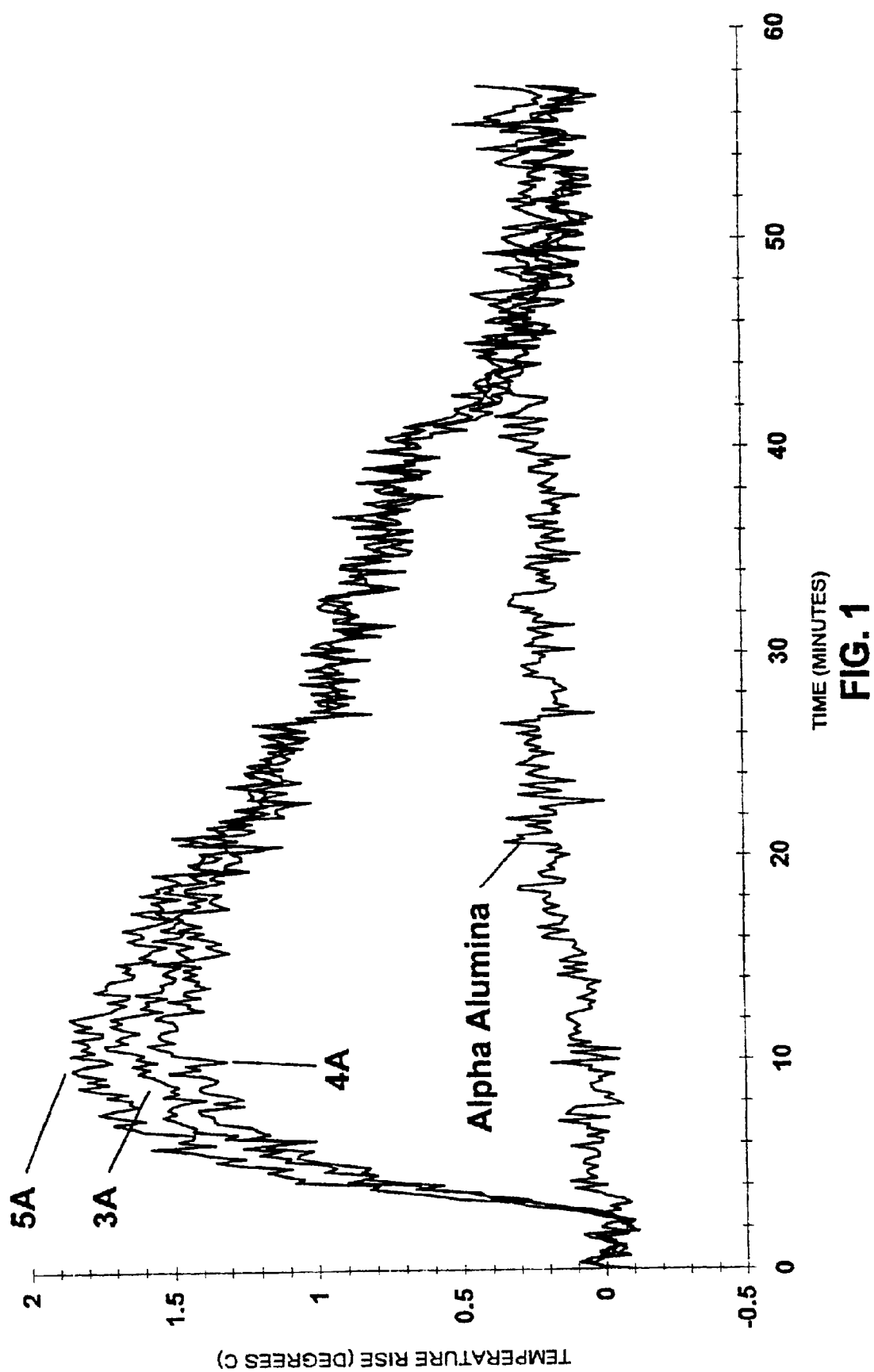
FIG. 1 is a plot of temperature versus time of four solids measured in Example 1.

As discussed previously, the invention is a method for determining at least one surface property of a solid or a mixture of solids. The invention is most beneficial when applied to a plurality of six, twelve, or more solids or mixtures of solids such as those typically found in combinatorial chemistry applications. For example, an array of solid materials may be synthesized using a combinatorial approach. It would be desirable for the solids in the array to be evaluated in at least groups, as opposed to the traditional one-by-one sequential approach. With the rate of combinatorial solid synthesis being high, the traditional evaluation approach would create a significant bottleneck. The method of the present invention allows for virtually simultaneous measurement of radiation corresponding to multiple solids from which at least one surface property of each solid can be determined.

The plurality of solids or mixtures of solids to be evaluated contains at least two different solids or mixtures of solids, but can contain hundreds or thousands of different solids or mixtures of solids. Preferred arrays contain the number of solids or mixtures equivalent to the numbers commonly employed in combinatorial chemistry methodology, such as 48, 96, 192, or 384 different solids or mixtures of solids. The solid(s) may be commonly known solids or may contain novel materials being investigated. It is contemplated that the present method may be used to determine a surface property of solids such as inorganic solids, organic solids, catalysts, adsorbents, polymers, ceramics, metals, and various types of carbons. Examples of classes of such include zeolites, molecular sieves, aluminas, silicas, amorphous silica aluminas, zirconias, mixed metal oxides, clays, ion exchange resins, and polymers including functional polymers. The plurality of solids to be evaluated may be comprised of a plurality of individual solids, a plurality of mixtures of solids, or a plurality containing both individual solids as well as mixtures of solids. Furthermore, within the plurality of solids there may be replicates of the same solid or mixture of solids. It may be helpful to include one or more known solids in a plurality containing novel or unknown solids. When the term "solid" is used herein, it is meant to include the situation where the "solid" is a mixture of two or more solids as well as when the "solid" is an individual solid material.

The plurality of solids or mixtures of solids are placed on at least one support. Preferably, the support comprises one or more plates having a plurality of wells to retain the solid particles. However, various other support designs may be used such as a honeycomb or a substrate with patches or spots of solid material. The support is preferably constructed of an inert material such as a clay, a ceramic, carbon, plastic or non-reactive metal, slate, metal oxide, or combinations of the foregoing. Particularly preferred are ceramic, stainless steel, and slate. The support is preferably constructed to be able to transfer heat to the plurality of solids in a reproducible manner. The support may be associated with one or more heaters. The heaters may be block heaters, individual heaters, heating tape, radiant heater, heat exchanger, laser, suppository heaters, and the like. Heaters such as the microfabricated hotplates of U.S. Pat. No. 5,356,756 B1, herein incorporated by reference, may also be employed. The arrangement of the support and the heater may be such that all of the solids in the array are heated together, at the same rate, and to the same temperature. In another embodiment, however, each individual solid or mixture of solids is individually heated.

The solids or mixtures of solids making up the array of solids may be deposited onto one or more supports by any convenient known technique such as pipetting, absorb stamping, silk screen, solid deposition, slurried, or manually transferred. In a preferred embodiment, the deposition process would be conducted robotically similar to that used to load multi-cell plates in biochemical assays. Several separate depositions may be used to deliver the solids or mixtures of solids to the support(s). For ease of relative comparisons, it is preferred that the quantity of each of the solids or mixtures of solids to be tested is the same or nearly the same, or that the quantity of each of the solids is measured. Under certain conditions, however, the technique may be insensitive to material quantity.

One or more supports containing the array of solids or mixtures of solids are placed in a chamber. The chamber may be sealed to prevent leaks and the chamber is equipped with conduits to flow at least one stream through the chamber to contact the plurality of solids. It is preferred that the conduits be equipped with a flow meter or other such device to regulate or measure the amount of fluid passing through the conduit. In a typical embodiment, the stream would be comprised of a carrier fluid and one or more adsorbate. Valving would allow different streams to be introduced to the chamber. For example, an inert fluid may be flowed through the chamber during a pretreatment portion of the process, and then the carrier fluid and adsorbate may be flowed during another portion of the process. While it is preferred that the invention be operated on a flowing basis with adsorbate compound(s) flowing by or through the solids under adsorption conditions, batch evaluations such as in a stirred autoclave or agitated container can be employed particularly in biological situations. It is understood that, because of the investigative nature of the method and the variety of solids that may be under investigation, the general term "adsorbate" refers to a fluid that may be adsorbed by one or more of the solids. In fact, however, one or more of the solids in a plurality may not interact with the "adsorbate" at all, and so the term "adsorbate" as used periodically herein is meant to include fluid with the potential or possibility of being adsorbed by the solids. It is not required that the solids actually adsorb the adsorbate. Temperature ranges or ramp rates, pressure ranges or ramp rates, space velocities, and other conditions will be dependent on the solids being evaluated and the adsorbate(s) used.

As discussed below, one specific embodiment of the invention involves controlled heating of the solids during or after contacting with an inert fluid. Therefore, it is preferred that the chamber is equipped with a heater and heater controls to heat the solids contained within the chamber. It is desirable that the chamber is also equipped with apparatus to independently monitor the temperature of the samples within the chamber. In another specific embodiment of the invention, controlled pressure ramping is used, and so the chamber may be equipped with apparatus for maintaining and controlling pressure.

In alignment with the chamber is a detector used to detect radiation associated with the solids or mixtures of solids of the plurality. The measurements made using the detector may involve radiation emitted, absorbed, or altered by the solid. Examples of suitable techniques used to obtain the measurements include ultraviolet spectroscopy, visible spectroscopy, fluorescence, infrared thermography, nuclear magnetic resonance, electron paramagnetic resonance, x-ray adsorption, x-ray photoelectron spectroscopy, Raman spectroscopy, and combinations thereof. Furthermore, one or more detectors of the same or different types may be used simultaneously. In a preferred embodiment of the invention, discussed in detail below, infrared thermography is employed. In the preferred embodiment, infrared thermography is a process wherein infrared radiation of the solids is emitted in the form of heat and is detected and spatially mapped resulting in a three-dimensional "picture" called a thermogram or thermal image. The thermogram is directly related to the temperature of the objects. Sequentially collected thermograms allow for a determination of temperature versus time as well.

A microprocessor is very often used as a data collection device and employed in the determination of one or more surface properties from the measured infrared data. A wide variety of surface properties, characteristic of the surface or boundary of a material may be determined. Such a determination may be qualitative or quantitative, or the result may be compared on a relative basis among a set of solids. Examples of surface properties include the number of acid sites, acid site distribution, acid site energy or acid site strength, acid site strength distribution, base site strength, number of base sites, base site distribution, base site strength distribution, base site energy or base site strength, porosity, pore size, pore density, pore volume, pore shape, surface area (both micropore and non-micropore), metal dispersion, exposed metal surface area, mobility of metals on the surface of a solid, chemisorb properties, physisorb properties, adsorption selectivity, desorption selectivity, ion-exchange capacity, and combinations thereof. Multiple surface properties may be determined from one set of measured data, or a single surface property may be determined. The present invention is designed to measure a surface property of at least one solid. That measurement may then be used to predict how a solid would behave in a particular application. For example, if the solid is to be used as an adsorbent, the pore size and pore density may be important factors in the identification of potential successful adsorbents. Also in the case of an adsorbent, the ability of a solid to physisorb or chemisorb one or more compounds may be quantitatively or qualitatively measured using the present invention resulting in indications as to which solids would be most successful in a particular application. When the solid is to be used as a catalyst in an application, the surface property determined in the present invention may indicate whether the catalyst would be successful in the particular application. For example, a solid having a high acid site strength may have greater catalytic activity. Note that in the case of catalysts, the reaction of the ultimate use of the catalyst need not be performed to gain information as to whether a catalyst would be successful. A surface property is determined for the solid, and known relationships between surface properties and catalytic activity lead to the conclusion as to which of the solids may perform as a catalyst in a given application.

In one embodiment of the invention, termed "the adsorption mode embodiment," the plurality of solids or mixtures of solids are placed on at least one support and the support is housed in a chamber having conduits for the flow of fluid through the chamber. The chamber is closed and sealed, and a fluid is contacted with the solids under isothermal conditions. The fluid, which may be liquid or gas phase, is generally selected to contain an adsorbate that is expected to be adsorbed by one or more of the solids in the plurality. The adsorption interaction between the solids and the adsorbate may take a variety of forms such as, for example, physisorption or chemisorption of the adsorbate onto the solid. The fluid-solid interaction may cause a change in the radiation detected, perhaps an increase or decrease in the amount of emitted or adsorbed radiation or perhaps another alteration of the radiation. The change in the radiation is detected and measured, and from those measurements a surface property of the solids may be determined.

In another embodiment of the invention, termed "the desorption mode embodiment", the radiation may be monitored as the adsorbate is desorbed from the solids. In this embodiment, the adsorbate is contacted with the solid(s) for a period of time. An inert fluid is then introduced and the adsorbate is desorbed from the solid(s) while the radiation is monitored. The desorption may be accomplished by techniques such as ramping the temperature or the pressure. Any change in the radiation being monitored during the desorption is measured and recorded. Again, a surface property of the solids may be determined from the measured change in the radiation during the desorption of the adsorbate from the solids.

In one specific embodiment, relative adsorptivity may be measured by contacting a carrier fluid containing at least one adsorbate with an array of solids on a support. Depending on the application, a heater may be associated with the support. The relative adsorptivity of each solid or mixture of solids in the array is detected by sensing the radiation emitted, adsorbed, or altered, by the respective solids. Solids having the greatest relative thermal event, such as exotherm or endotherm, may then be identified since a large detected exotherm may be indicative of a solid having a high relative adsorptivity for a particular adsorbate. The radiation measurements may be taken while the adsorbate is contacting the array of solids, or while the adsorbate is being desorbed from the solids. The process may be conducted isothermally, at a single temperature, or the temperature may be ramped over a predetermined range of temperatures. Usually the isothermal technique is employed when the radiation is measured during the contacting of the adsorbate with the solids (the adsorption mode embodiment), and the temperature ramping conditions are used when the radiation is measured during the desorption of the adsorbate from the solids (the desorption mode embodiment). Similarly, the process may be conducted at a constant pressure, or the pressure may be ramped. In the adsorption mode embodiment, a constant pressure would be preferable. In the desorption mode embodiment, the pressure may be ramped lower to cause the desorption of the adsorbate from the solid(s) as an alternative to ramping the temperature. The radiation data is collected and plotted versus time. Monitoring the radiation under temperature or pressure ramping conditions not only allows the determination of the acid site distribution of a solid, but also the strength of the detected sites. For example, viewing a plot of the temperature versus time for infrared thermography data, the relative area of the deviation from the temperature ramp program may indicate the acid site distribution. The position of the deviation on the overall curve, or either the temperature axis or the time axis, may indicate the strength of the detected sites Alternatively, the power requirement of the temperature controllers may be monitored during adsorption or desorption. The temperature of the solids would be monitored by, for example, infrared thermography and that temperature signal would be used as the temperature input for the heating s element controllers. The resulting power requirement data collected during adsorption or desorption would be plotted versus time as shown in Example 5. One or more surface properties could be determined from the resulting data.

Certain adsorbate compounds may be more beneficial than others in determining a particular surface property. A carrier gas containing water, for instance, may be used as an indicator of the ability of a solid to physisorb water, while a carrier gas containing pyridine may be used as an indicator of the acid site distribution of a solid. A specific adsorbate may comprise the entire fluid, or may be just a small portion of the fluid. Additional examples of suitable fluids include ammonia, hydrogen, nitrogen, air, helium, argon, alkanes including methane, fluorine, neon, amines including alkylamines, quinoline, carbon monoxide, carbon dioxide, carboxylic acids, alkynes, alkenes, alcohols, aromatics, thiols, esters, ketones, aldehydes, esters, amides, nitrites, nitroalkanes, and many others. The adsorption of at least one component of the fluid onto the solid has associated heat that is emitted and detected by the Infrared detector. Similarly, the desorption of at least one component of the fluid from the solid results in a change in the radiation detected. From the infrared measurements, a surface property of the plurality of solids may be determined. Classes of solids may also be distinguished from one another by this method, see Example 1.

Similarly, multiple adsorbates of varying sizes may allow for a detailed calculation of the pore volume distribution of solids. Pore volumes of solids such as zeolites have been previously measured by measuring the mass of adsorbates, such as lower alkanes, which physisorb and condense on or in the zeolites. The density of the hydrocarbon, at a selected standard condition, allows for the calculation of pore volume or pseudo pore volume. In the present invention, because there is heat associated with physisorption and condensation, the measurement of the temperature change of a material may be related to the amount of adsorbate that is adsorbed, has condensed, and is filling the pores of a material. The temperature change is correlated to pore volume and the use of multiple adsorbates of varying sizes allows for the calculation of a pore volume distribution. The accessibility to the entire volume of pores is restricted to the smaller adsorbate molecules. By way of example, a plurality of samples may be brought to a temperature, T, and an inert gas containing some partial pressure of a lower alkane believed to be accessible to the entirety of pores is equilibrated with the solids. The temperatures of the solids are monitored using infrared thermography during the equilibration. Any temperature rise accompanying the adsorption and condensation allows for a relative comparison of the sample total pore volume or an absolute measurement against a standard. The array of solids may be further probed by progressively larger adsorbates to generate the pore volume distribution. When the progression of adsorbates is from smaller adsorbates to larger adsorbates, the solids may require treatment to remove a smaller adsorbate before exposure to a larger adsorbate. Of course, it is also possible to begin with a larger adsorbate and employ progressively smaller adsorbates. In the latter case, the progressively smaller adsorbates may be used sequentially without treating the solids between adsorbates. This example was described in the adsorption mode embodiment, and it should be understood that the same technique could be used in the desorption mode embodiment as well.

In general, it is preferred that the solids in an array of samples to be analyzed are "activated" or preheated to a set temperature in an inert atmosphere. The solids are then cooled to the temperature under which the primary steps of the invention are to be performed or to the starting temperature of a temperature ramp. Activation may operate to desorb extraneous compounds from the solids, thus aiding in an accurate reproducible determination of a surface property. It is further preferred that the inert atmosphere is a flowing inert fluid so that compounds desorbed from the solids are removed and not reabsorbed when the solids are cooled.

In yet another embodiment of the invention, the adsorbate stream may be contacted with the array of solids in a pulsed manner. Infrared images, for example, would be collected while the pulses of the adsorbate are being contacted with the solids. Pulsing allows for the chemical reaction or adsorption at active sites, but minimizes the diffusion of the heat generated or consumed throughout the material. Thus pulsing allows for a more detailed thermographic map of the material surface as compared to that obtained under continuous adsorbate contacting conditions. A topographical map approaching the level of resolution of the infrared thermography system may be generated, see EXAMPLE 6.

Illustrative of the present invention would be using a probe molecule and infrared thermography to determine the quantity of Bronsted acid sites in the samples of a combinatorial array. Alkylamines such as ethylene, n-propylamine, and tertbutylamine have been shown to adsorb one-to-one on the Bronsted acid sites of zeolites such as ZSM-5 in the hydrogen form, ZSM-22 in the hydrogen form, zeolite Y in the hydrogen form, and ferrierite. Other materials such as silicas, aluminas, amorphous silica aluminas, metal oxides and mixed metal oxides may be similarly investigated. The desorptive temperature range has been found to be independent of the Bronsted acid site strength and a function of the alkylamine type only. The desorption is concurrent with the decomposition of the alkylamine which forms an alkene and ammonia.

Traditionally, these products are sequentially quantified by mass spectrometry and the number of Bronsted acid sites are assigned accordingly, with one Bronsted acid site attributed to each ammonia or alkene detected. The Bronsted acid sites associated with the cavities and channels of multidimensional zeolites have been distinguished by the use of amines with select kinetic diameters, see Palkhiwala, A. G., Gorte, R. J. Catal. Lett. 57, No. 1,2 (1998) p. 19–23 which uses temperature programmed desorption of n-propylamine to quantify the number of Bronsted acid sites on the zeolite ferrierite. Decomposition of n-propylamine is reported to be catalyzed by Bronsted acids in the temperature range of about 300° C. to about 375° C. The mechanism of the reaction is a Hoffman elimination, which is a reaction not catalyzed by Lewis acids. The alkylamines would remain adsorbed on the Lewis acid sites until temperatures higher than 375° C. are reached. Therefore, this reaction is appropriate for selective screening of materials with Bronsted acidity, similar to zeolites. The location and accessibility of the Bronsted acid sites were also quantified on ferrierite by the choice of appropriate probe molecules. For example, it was observed that n-propylamine could access the acid sites within eight-membered-ring pore systems, while isopropylamine could not. Through comparing temperature-programmed-desorption using n-propylamine and temperature-programmed-desorption using isopropylamine, the number of acid sites within the eight-membered-ring pores could be quantified.

The present invention allows equivalent results to be obtained where the samples are analyzed in parallel through monitoring the energy change occurring with the decomposition reaction using, for example, infrared thermography. Because the decomposition temperature is independent of the Bronsted acid site strength, the overall energy associated with the decomposition desorption is expected to be substantially equivalent at each site and for each material contained in an array. Given an array of materials with approximately equivalent heat capacities, the response, or temperature change, of each material to desorption from the Bronsted sites should be equivalent. This equivalency should allow for a direct comparison of the material making up an array when the temperature change accompanying desorption is monitored by infrared thermography. In, short, the number of Bronsted acid sites of each sample should be proportional to the temperature change accompanying desorption. Responses may also be quantified against internal standards or reference materials.

A specific example of the desorption mode embodiment of the present invention involves the determination of the number of Bronsted acid sites in an array of samples and may be conducted as follows. The array of samples may be first activated (discussed below) and then brought to a temperature "T". The array is contacted with a carrier gas containing a selected amine compound. The acid sites of the samples adsorb the amine compound. A temperature ramp is applied and the physisorbed species would desorb at about 200° C., followed by the decomposition reaction of the amine at a higher temperature, such as about 300° C. to about 375° C. for n-propylamine. The temperature profile as determined by infrared thermography for each sample is subtracted from a background profile of the activated array. The resultant profile would indicate the endotherms associated with the desorptive process and thus provide a measure of the Bronsted acid sites of each of the samples in the array. In a more specific embodiment of the invention, the quantity of Bronsted acid sites in different sized regions of the samples in the array may be determined using select probe compounds and comparing resultant temperature profiles. Differences in the temperature profiles with different probe molecules will indicate where a quantity of Bronsted acid sites is located on a sample.

Still another specific embodiment of the invention is a method which quantifies the dispersion of metal loaded on materials such as zeolites and silicas, aluminas, and amorphous silica aluminas. Infrared thermography is used to measure the exposed metal surface area of supported metal catalysts, and this information is used to quantify the dispersion of the metal loading and to measure changes in exposed surface area between fresh and used catalysts. Typically the exposed metal surface area on supported metal catalysts is found by chemisorbing a gas such as hydrogen, carbon monoxide, or oxygen and measuring the uptake that occurs under conditions that allow coverage corresponding to a monolayer. The exposed metal surface area can be determined using the adsorption stoichiometery, the number of surface atoms covered for each adsorbed molecule, and the number of metal atoms per unit surface area. Pressure-volume relationships are typically used to determine the uptake. After the mass of the metal on the sample is known, the dispersion, or metal surface area per unit mass metal, can be determined. In the present invention, the heat associated with chemisorption may be monitored using infrared thermography to measure the temperature change of the solid materials. The temperature change may then be related to the amount of uptake of the adsorbate gas. For example, a plurality of supported platinum catalysts each having the same loading of platinum, but prepared by different methods, may be activated in a chamber as described above. With the chamber and the solids at an initial temperature, an inert gas having a selected partial pressure of hydrogen is equilibrated with the solids. The temperature of the solids is monitored using infrared thermography during the equilibration. The temperature rise accompanying the adsorption of the hydrogen on the platinum surface allows for a relative comparison of the sample surface areas and the dispersion. For more quantitative determinations, comparison to standards may be performed.

Figure 12:
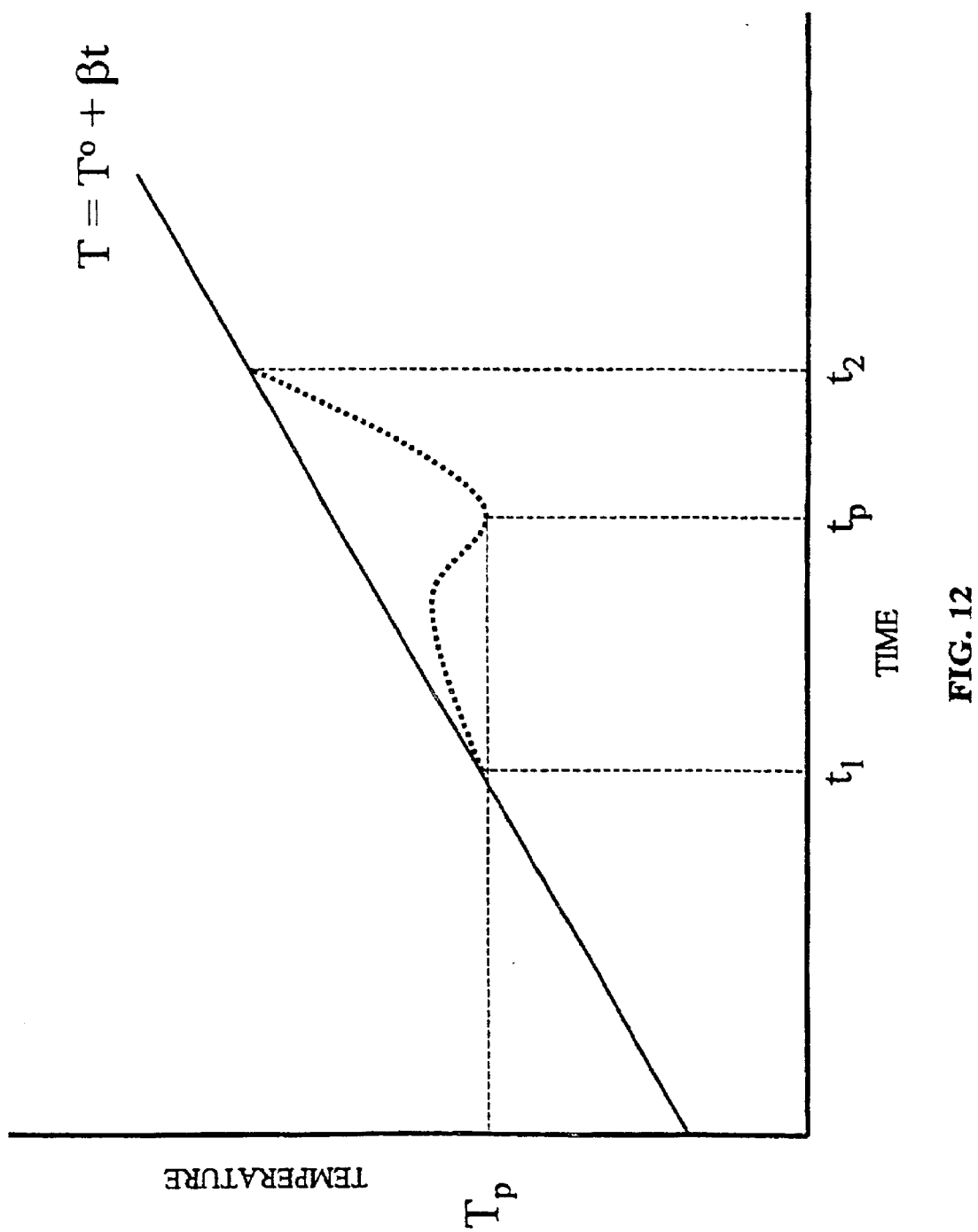
FIG. 12 is a generic example of hypothetical data plotted as temperature versus time showing a deviation of the ramp rate when an adsorbate is desorbed from a solid.

In addition to determining relative surface properties among the samples of an array, the present invention may be used to directly determine the number of adsorption sites and the heat of adsorption, assuming the desorption is not an activated process. If the desorption is activated, the activation energy for desorption is determined. Specifically, after adsorption of a species "A" and then heating with a fixed heat input profile with respect to a "blank" run, resulting in a ramp rate "$\beta$", a deviation from the ramp rate is seen in the plot of the infrared thermography data caused by desorption, see FIG. 12. This temperature profile can be described numerically in various ways. As a specific example, it can be described as $$T = T^0 + \beta t - \sum_{i=0}^{n} a_i t^i$$

which is a polynomial description where "T" is temperature, "t" is time, "$a_i$" is the "i"th coefficient in the polynomial expression for the temperature deviation, and "i" is an integer ranging from zero to "n" where (n+1) is the appropriate number of terms in the equation to accurately describe the behavior. "$N_A$", the total number of moles of "A" adsorbed in the surface of the solid, can be calculated from:

$$N_A = \int_{t_1}^{t_2} \sum_{i=0}^{n} a_i \cdot t^i \cdot \frac{C_{ps}}{\Delta H} dt \quad (1)$$

Where "$C_{ps}$" is the specific heat of the solid, "$\Delta H$" is the heat of adsorption of "A" expressed in joules per mole of "A", "T" is the temperature and "t" is time. In most cases, "$\Delta H$" has to be determined, however. Assuming Langmuir adsorption, one can describe desorption as:

$$-\frac{dN_A}{dt} = v \cdot N_A^m \exp\left(-\frac{E_d}{RT}\right) \quad (2)$$

Where "$N_A$" is the total number of "A" adsorbed in the surface of the is solid, "v" is the frequency factor, "m" is the desorption order, "$E_d$" is the activation energy for desorption which tends to coincide with the adsorption heat since adsorption is typically not an activated process. Langmuir-type desorption assumes the existence of identical and independent desorption sites, as well as an absence of interaction between the adsorbates. However, Equation (2) can be redefined for non-Langmuir situations. Any extrapolations of this method to non-Langmuir situations would be readily understood by one of ordinary skill in the art. Combining the polynomial description of "T" and Equation (2), it can be shown, since $d/dt(-dN_A/dt)=0$ at the peak, that:

$$\frac{d}{dt}\left(v \cdot N_A^m \exp\left(-\frac{E_d}{RT}\right)\right) = \quad (3)$$

$$v \cdot \exp\left(-\frac{E_d}{RT}\right) N_A^{m-1} \cdot m \cdot \frac{dN_A}{dt} + v \cdot N_A^m \cdot \exp\left(-\frac{E_d}{RT}\right) \cdot \frac{E_d}{RT^2} \cdot \frac{dT}{dt} = 0$$

$$\text{where } \frac{dT}{dt} = \beta - \sum_{i=1}^{n} a_i \cdot t^{(i-1)} \cdot i / t_p \text{ or}$$

$$-v \cdot m \cdot N_A^{(m-1)} \cdot \exp\left(\frac{-E_d}{RT_p}\right) + \frac{E_d}{RT_p^2}\left[\beta - \sum_{i=1}^{n} a_i \cdot t^{(i-1)} \cdot i\right] / t_p = 0 \quad (4)$$

In Equation (4) "$N_A$", "m", "v" and "$E_d$" are unknown. "v" can generally be assumed as $10^{13}$ Hz, "$t_p$" is the time at which the extremum is observed. Selecting a value for "v" would not generally affect the ranking. "m" can be derived from a plot of $\ln[(-dN_A/dt)/N_A^m]$ vs 1/T for different "m". For the correct "m", the plot will be linear.

In most cases, first order Langmuir desorption describes the behavior well. In such a case, "m"=1, "v"=$10^{13}$ Hz, Equation (4) reduces to:

$$-10^{13} \cdot \exp\left(\frac{-E_d}{RT_p}\right) + \frac{E_d}{RT_p^2}\left[\beta - \sum_{i=1}^{n} a_i \cdot t_p^{i-1} \cdot i\right] \quad (5)$$

In which all but "$E_d$" are known. Solving Equation 5 provides "$E_d$" and assuming $E_d \approx \Delta H$, Equation (1) then gives "$N_A$".

In a more general description, the deviation from the ramp rate in the plot of the infrared thermography data can be fitted to functional form f(t). The expression would be a function of time, and in general terms can be referred to herein as f(t). Equations (3), (4), and (5) above would therefore respectively become:

$$N_A = \int_{t_1}^{t_2} f(t) \cdot \frac{C_{ps}}{\Delta H} dt \quad (1')$$

$$\frac{d}{dt} = \left(v \cdot N_A^m \exp\left(-\frac{E_d}{RT}\right)\right) = v \cdot \exp\left(-\frac{E_d}{RT}\right) N_A^{m-1} \cdot m \cdot \frac{dN_A}{dt} + \quad (6)$$

$$v \cdot N_A^m \cdot \exp\left(-\frac{E_d}{RT}\right) \cdot \frac{E_d}{RT^2} \cdot \frac{dT}{dt} = 0$$

$$\text{where } \frac{dT}{dt} = [\beta - f'(t)]/t_p$$

$$-v \cdot m \cdot N_A^{(m-1)} \cdot \exp\left(\frac{-E_d}{RT_p}\right) + \frac{E_d}{RT_p^2}[\beta - f'(t)]/t_p = 0 \quad (7)$$

$$-10^{13} \cdot \exp\left(\frac{-E_d}{RT_p}\right) + \frac{E_d}{RT_p^2}[\beta - f'(t)]/t_p \quad (8)$$

As described above, equations (7) and (1) can be used to determine "$E_d$" and "$N_A$".

The above discussion is directed mostly to Langmuir adsorption where "m" can be assumed to be equal to 1. However, the general method is also applicable to non-Langmuir adsorption, and in that case "m" could be derived from a plot of $\ln[(-dNA/dt)/NA m]$ vs 1/T for different "m", and for the correct "m", the plot will be linear (as discussed above). The value of "m" would be inserted in Equation 4, if the deviation can be described as a polynomial, or in Equation 7 if the deviation is not described as a polynomial. Equation 1' and Equation 4 or Equation 7 would be solved to determine "$E_d$" and "$N_A$".

Figure 9:
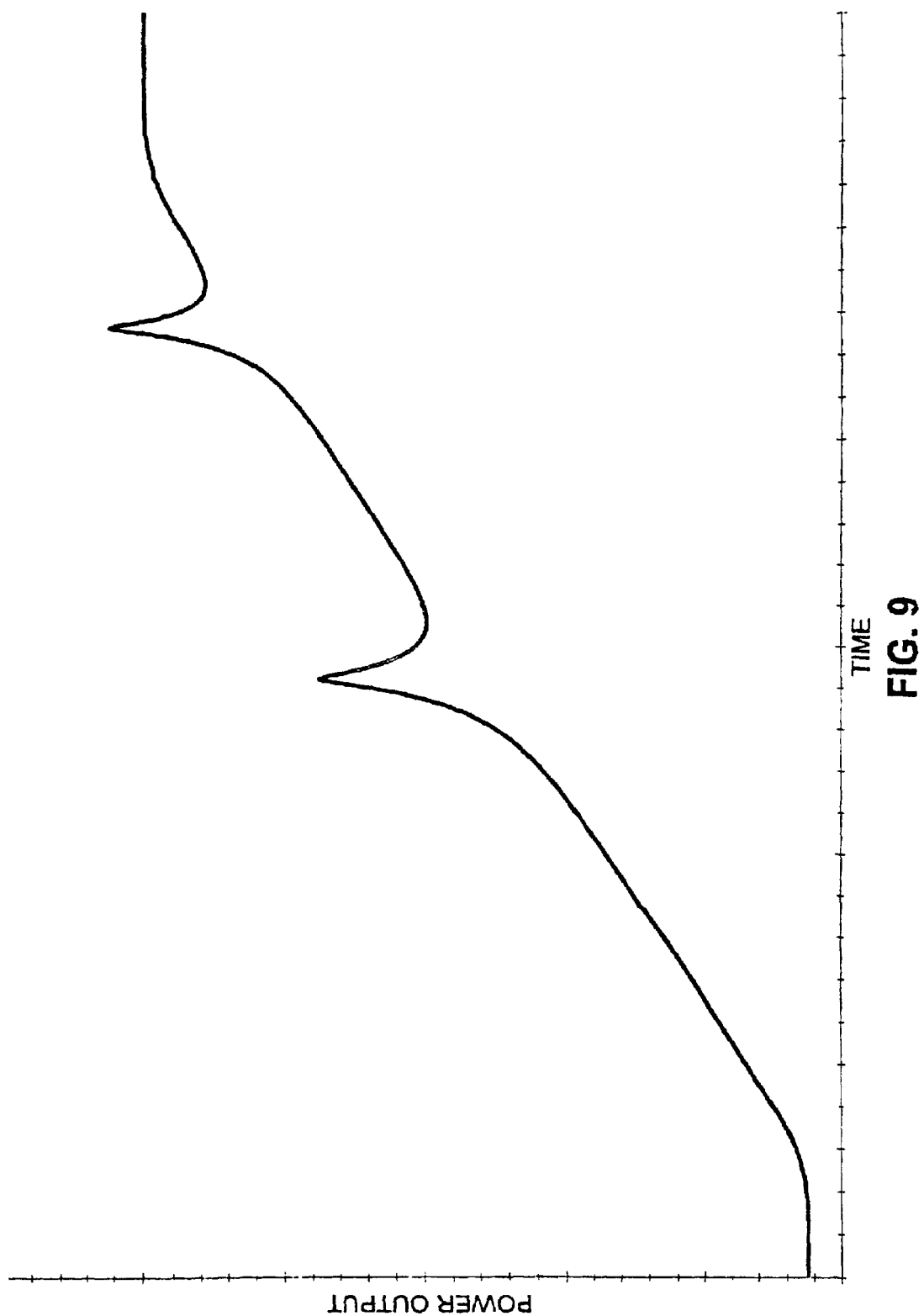
FIG. 9 is a plot of the temperature controller output data versus time where the temperature controller output data was collected after the solids were contacted with a fluid that may be adsorbed by the solids in Example 5.
Figure 10:
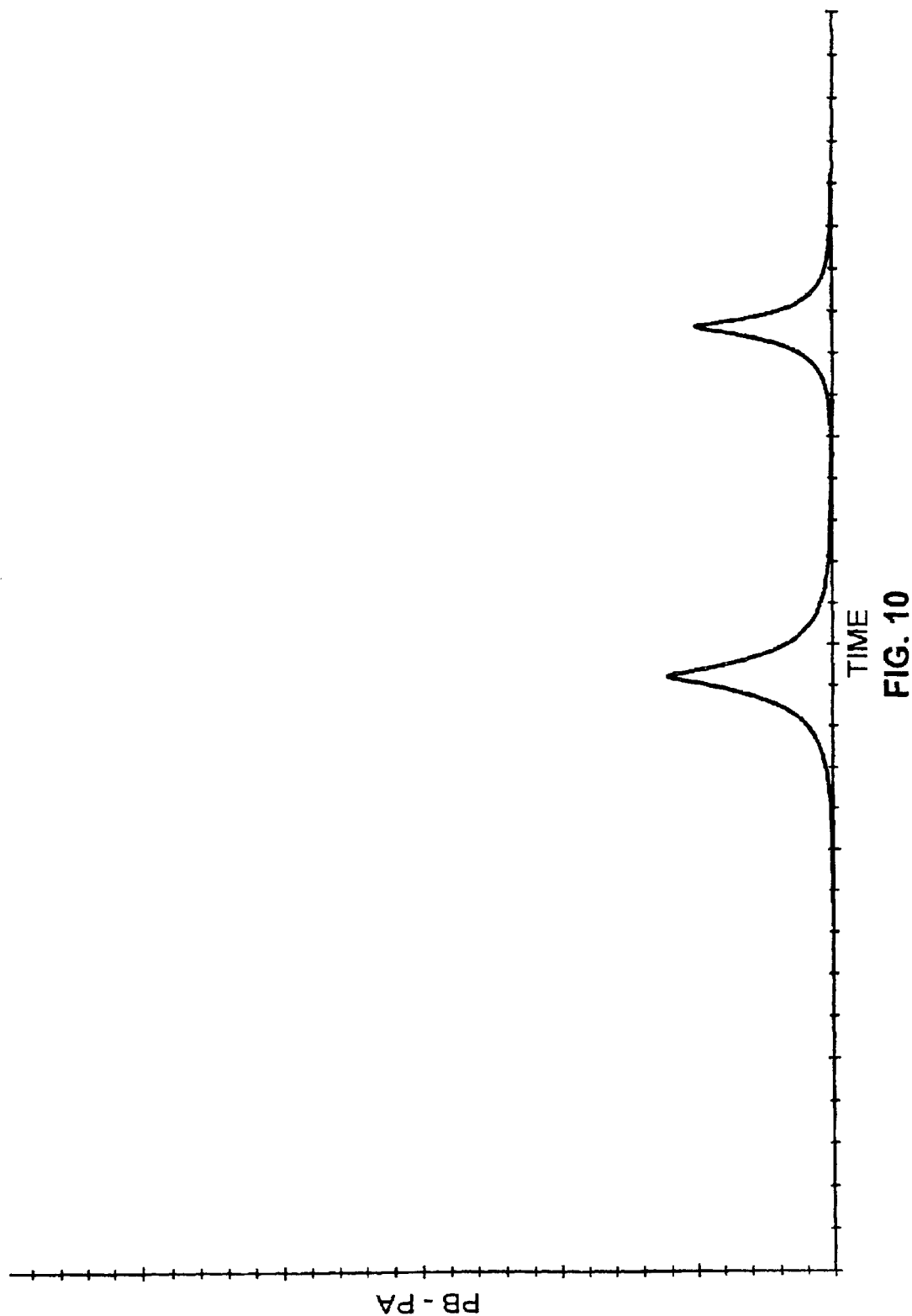
FIG. 10 represents the temperature controller output data of FIG. 8 subtracted from the temperature controller output data of FIG. 9 plotted against time. Each peak of FIG. 10 represents a quantity of fluid desorbing at a specific temperature.

In the discussion above, the experimental procedure provides for the heat input from the controller to be controlled according to a fixed profile. In an alternate embodiment, the experimental procedure may provide for the controller to attempt to attain the desired temperature ramp. The result would be a difference in heat input as shown in FIG. 9 and FIG. 10. This difference in heat input would be incorporated in calculations described above as follows:

$$N_A = \int_{t_1}^{t_2} \frac{f(t)' \cdot C_{ps}}{\Delta H} dt + \int_{t_1}^{t_2} \frac{(P_B - P_A)}{\Delta H} dt \quad (9)$$

Where "$(P_B-P_A)$" is determined from data such as that shown in FIG. 10. "$P_A$" is the heat input profile with time (which corresponds to the power output of the controller) during the experimental procedure, and "$P_B$" is the heat input profile with time during a blank run (i.e., no adsorbate). The formula reduces to:

$$N_A = \int_{t_1}^{t_2} \frac{f(t)' \cdot C_{ps} + (P_B - P_A)}{\Delta H} dt \qquad (10)$$

Where "f(t)" is measured and derived, "Cps" is known, "$(P_B-P_A)$" is measured and "$\Delta H$" is calculated using equations (7) and (10) as described above.

EXAMPLE 1

Twenty samples, including 3A, 4A, and 5A molecular sieves and alpha alumina, were placed In a chamber in the positions shown below. All samples were crushed and sieved to 60/40 mesh (200–420 $\mu$m).

|  | A | B | C | D |
|---|---|---|---|---|
| Row 1 | 5A | 5A | 5A | 5A |
| Row 2 | Alpha Alumina | Alpha Alumina | Alpha Alumina | Alpha Alumina |
| Row 3 | 3A | 3A | 3A | 3A |
| Row 4 | 4A | 4A | 4A | 4A |
| Row 5 | Alpha Alumina | Alpha Alumina | Alpha Alumina | Alpha Alumina |

In Row 1, the samples were all 50 mg, in Row 2, the samples were all 70 mg, and in Rows 3, 4 and 5, the samples were all 50 mg. The samples were dried at 300° C. for 1 hour. The chamber was brought to 30° C. under nitrogen purge at 1 LPM. Infrared thermography data acquisition began at t=0, and at t=2 minutes the nitrogen purge was discontinued and a humidified nitrogen stream was introduced. The humidified nitrogen stream had a dew point of 12.1° C. and was introduced at 1.2 LPM. At t=40 min. the humidified stream was discontinued and the nitrogen purge stream was reintroduced.

The temperature changes as indicated by infrared thermography were plotted versus time. Each temperature change for a given sample was calculated by subtracting the average of the respective initial ten temperatures recorded during the purge from the entire data set for the sample. The profiles for the 50 mg samples of Column D are shown in FIG. 1. The alpha alumina sample is clearly distinguished from the 3A, 4A and 5A molecular sieves.

EXAMPLE 2

Twenty samples, including dealuminated zeolite Y, a silica alumina molecular sieve, a fluorided solid having 75% SiO2 and 25% Al2O3, a solid having 75% SiO2 and 25% Al2O3, and alpha alumina, were placed in a chamber in the positions shown below. All samples were crushed and sieved 60/40.

|  | A | B | C | D |
|---|---|---|---|---|
| Row 1 | Dealuminated zeolite Y | Dealuminated zeolite Y | Dealuminated zeolite Y | Dealuminated zeolite Y |
| Row 2 | Silica alumina molecular sieve | Silica alumina molecular sieve | Silica alumina molecular sieve | Silica alumina molecular sieve |
| Row 3 | Fluorided silica alumina | Fluorided silica alumina | Fluorided silica alumina | Fluorided silica alumina |
| Row 4 | Silica alumina | Silica alumina | Silica alumina | Silica alumina |
| Row 5 | Alpha Alumina | Alpha Alumina | Alpha Alumina | Alpha Alumina |

In Rows 1–4, the samples were all 30 mg and in Row 5, the samples were all 50 mg. The samples were dried at 300° C. for 1 hour under flowing nitrogen. The chamber was brought to 30° C. under nitrogen purge at 1 LPM. Infrared thermography data acquisition began at t=0, and at t=2 minutes the nitrogen purge was discontinued and a pyridine-nitrogen stream was introduced at about 0.63 LPM. At t=35 min. the pyridine-nitrogen stream was discontinued and the nitrogen purge stream was reintroduced.

Figure 2:
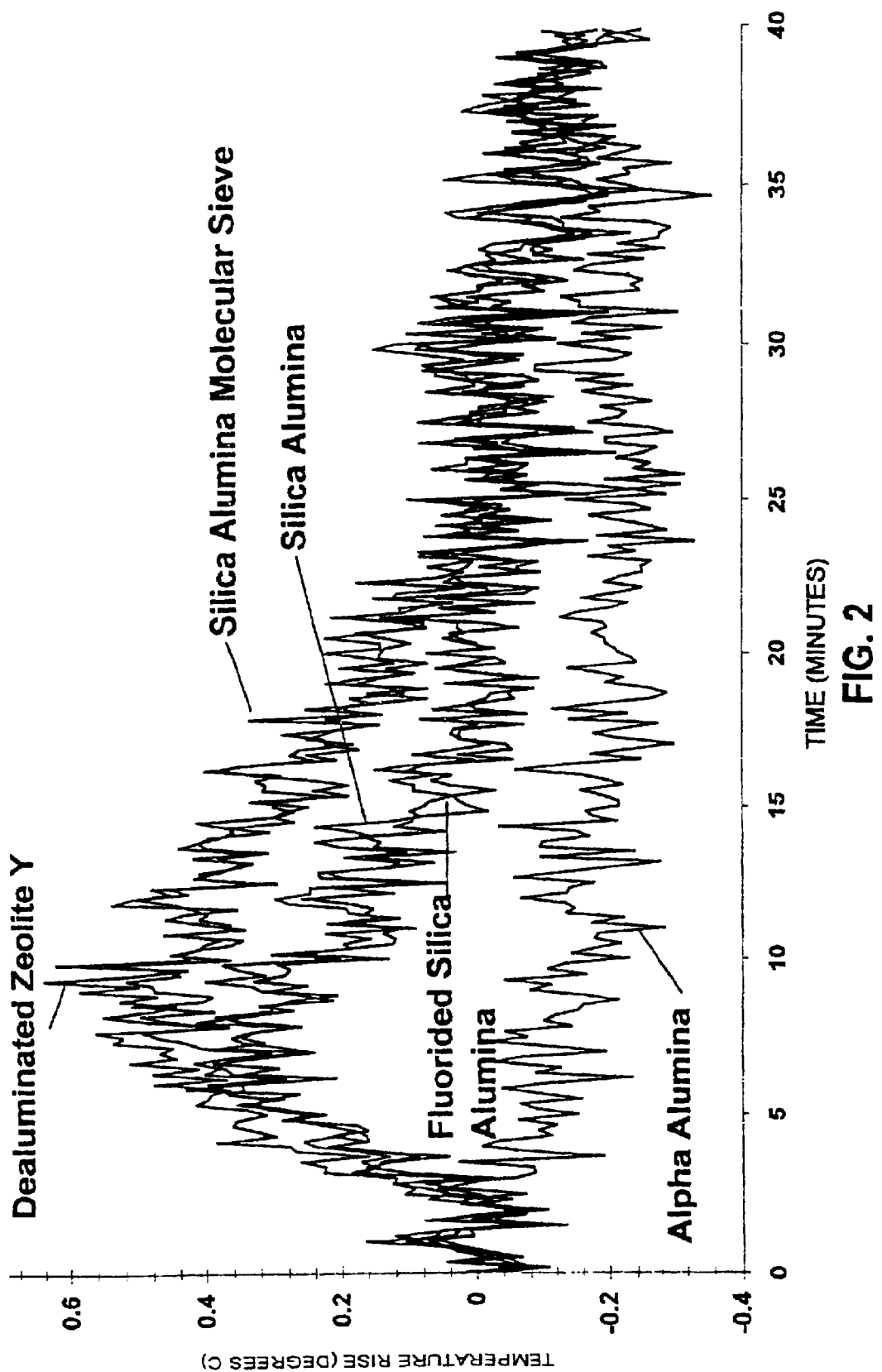
FIG. 2 is a plot of temperature versus time of four solids measured in Example 2.

The temperature changes as indicated by infrared thermography were plotted versus time. Each temperature change for a given sample was calculated by subtracting the average of the respective initial ten temperatures recorded during the purge from the entire data set for the sample. The profiles for the 50 mg samples of Column D are shown in FIG. 2. The profiles of FIG. 2 clearly show groupings of the different types of materials. The alpha alumina sample is clearly distinguished from the silica alumina materials which are also distinguished from the fluorided silica alumina materials.

EXAMPLE 3

Twenty samples, including 3A, 4A, and 5A molecular sieves and alpha alumina, were placed in a chamber in the positions shown below. All samples were crushed and sieved 60/40.

|  | A | B | C | D |
|---|---|---|---|---|
| Row 1 | 5A | 5A | 5A | 5A |
| Row 2 | Alpha Alumina | Alpha Alumina | Alpha Alumina | Alpha Alumina |
| Row 3 | 3A | 3A | 3A | 3A |
| Row 4 | 4A | 4A | 4A | 4A |
| Row 5 | Alpha Alumina | Alpha Alumina | Alpha Alumina | Alpha Alumina |

In Row 1 the samples were all 50 mg, in Row 2 the samples were all 70 mg, and in Rows 3, 4 and 5 the samples were all 50 mg. Beginning at 50° C., the chamber was ramped in temperature to about 260° C. under vacuum with infrared image acquisition. The chamber was cooled and opened and the samples were directly doused with liquid water. The chamber was closed and brought to 50° C. under vacuum. The chamber was held at these conditions for three hours to remove excess water. The temperature was then ramped from 50° C. to about 26° C. under vacuum with infrared image acquisition.

Figure 3:
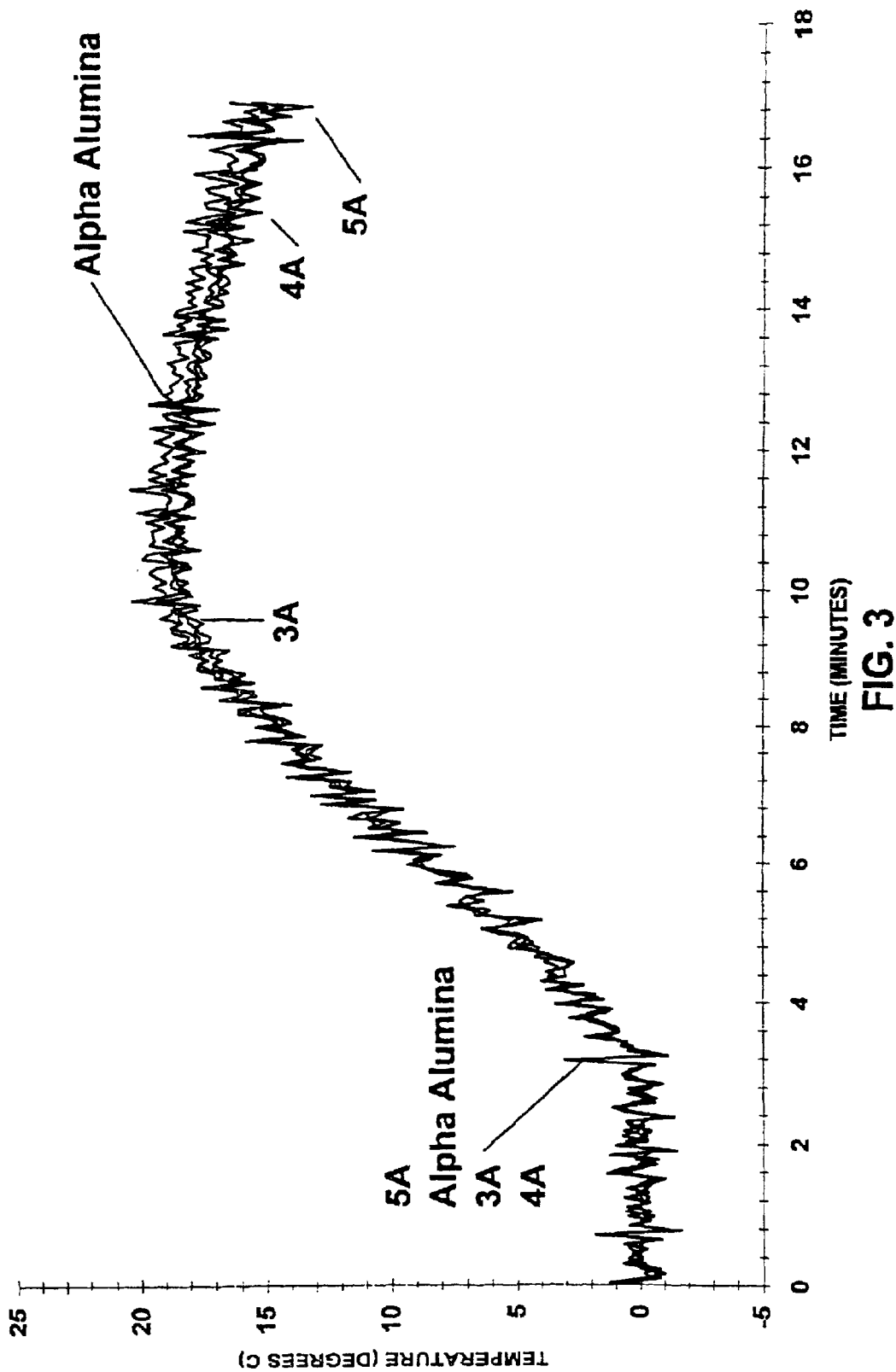
FIG. 3 is a derivative plot of the temperature versus time for four samples measured under dry conditions in Example 3.
Figure 4:
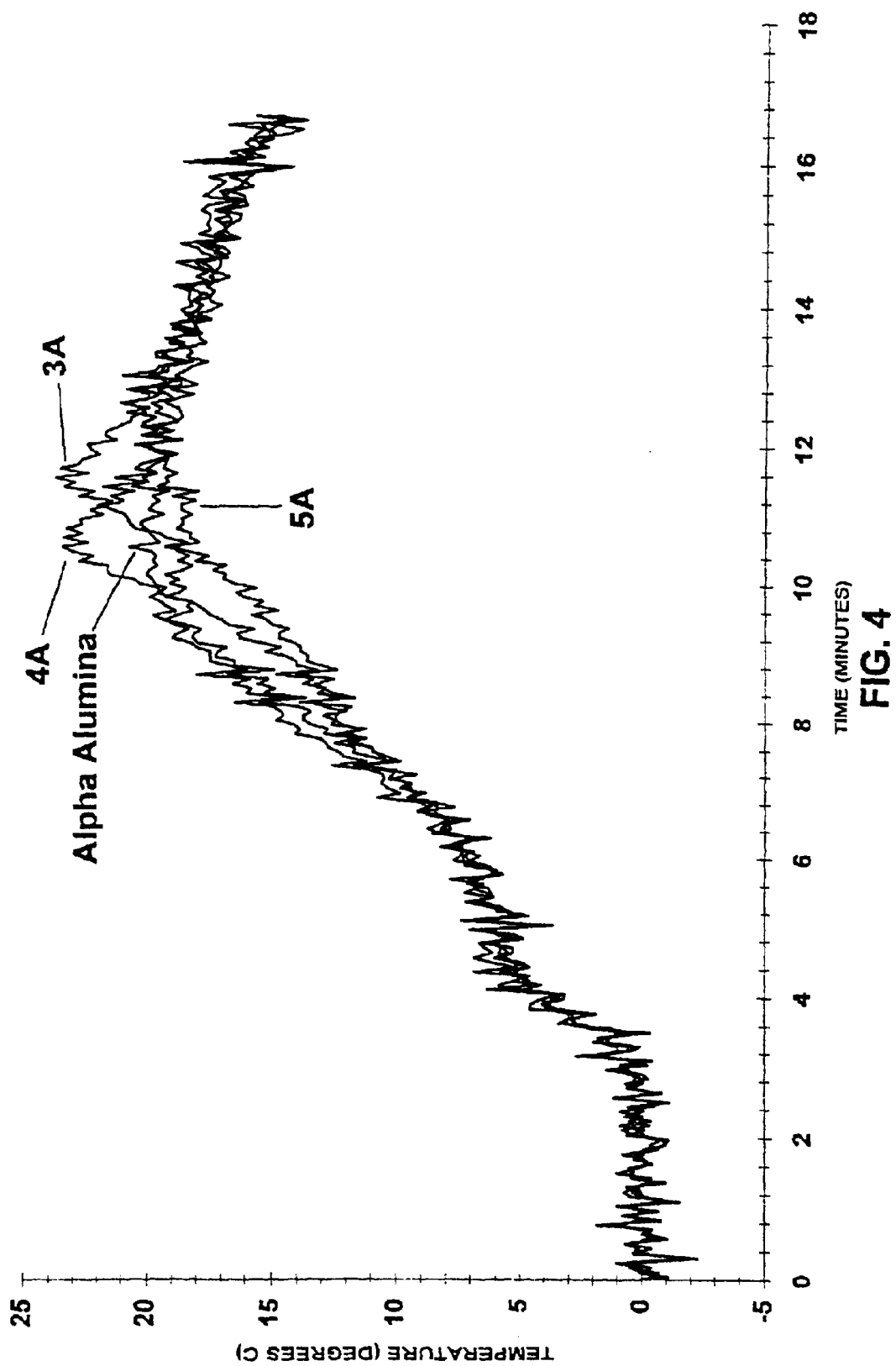
FIG. 4 shows the derivative plot of the temperature versus time for the four samples measured under wet conditions.

FIG. 3 shows the derivative profiles (dT/dt) of the temperature to versus time for the 50 mg samples of Column C as measured under the dry condition. FIG. 4 shows the derivative profiles (dT/dt) of the temperature versus time for the 50 mg samples of Column C as measured under the wet condition. The dry condition sample plots of FIG. 3 are almost identical until about nine minutes at which point the alpha alumina curve becomes distinct from the zeolite curves. The wet condition sample plots of FIG. 4 show distinct profiles for each of the four samples.

EXAMPLE 4

Figure 5:
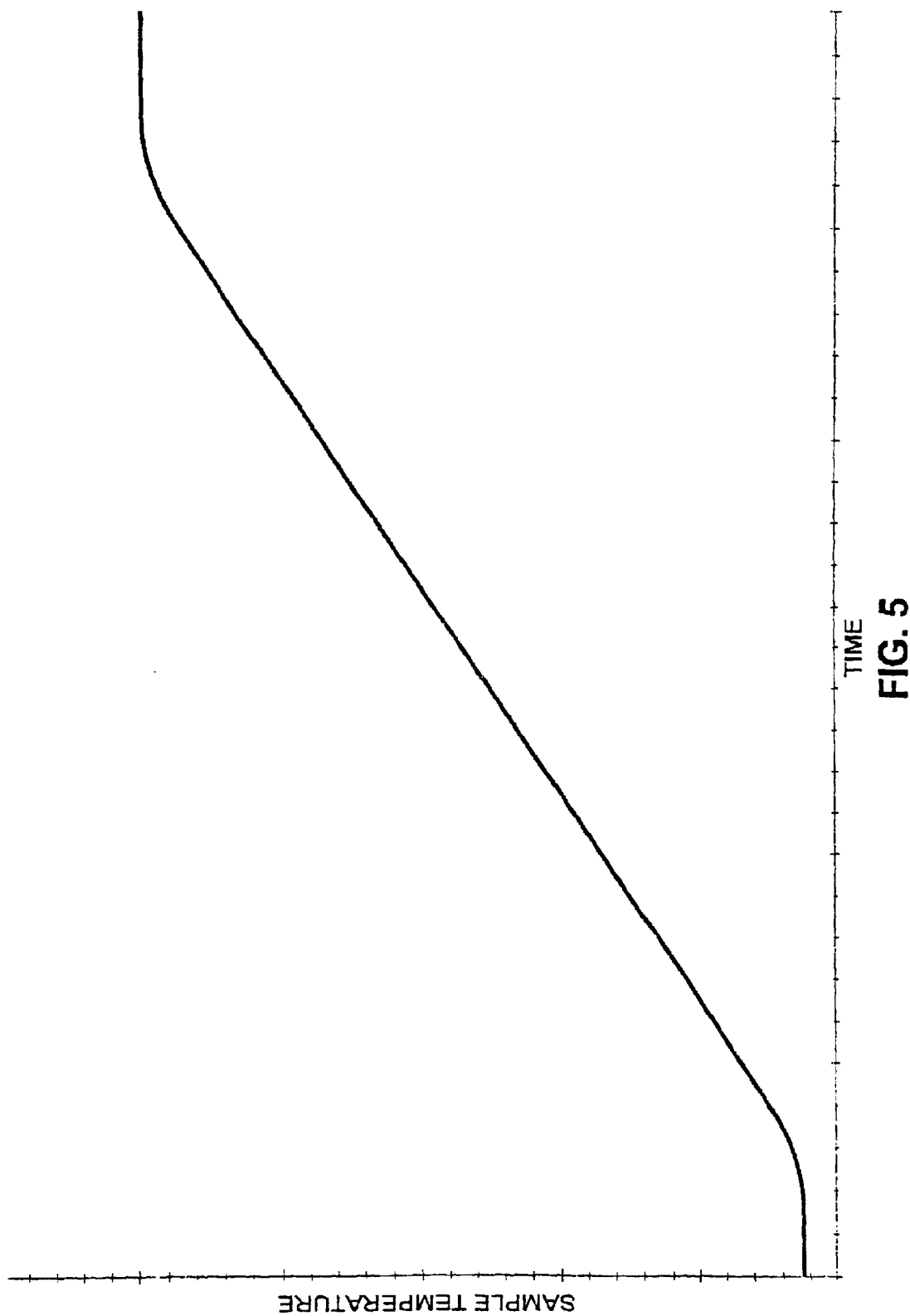
FIG. 5 is a plot of the temperature versus time of a single sample where the infrared thermography data was collected prior to the solids contacting a fluid that may be adsorbed by the solids in Example 4.

Samples would be placed in a chamber equipped with a heating device to ramp the temperature of samples from a first temperature to a second temperature. The method would be initiated at a first temperature, T1. Heat would be transferred to the sample array while an inert gas would be passed through each sample cell. Heat would be transferred until some specific region of the sample array reaches a predetermined end temperature, T2. The temperature (TA) versus time data would be taken using infrared thermography for each solid or mixture of solids in the sample array during the temperature ramp resulting in a baseline, called data set 1 and shown in FIG. 5. The above temperature ramp could be conducted in an inert atmosphere or conducted under flowing inert fluid.

Figure 6:
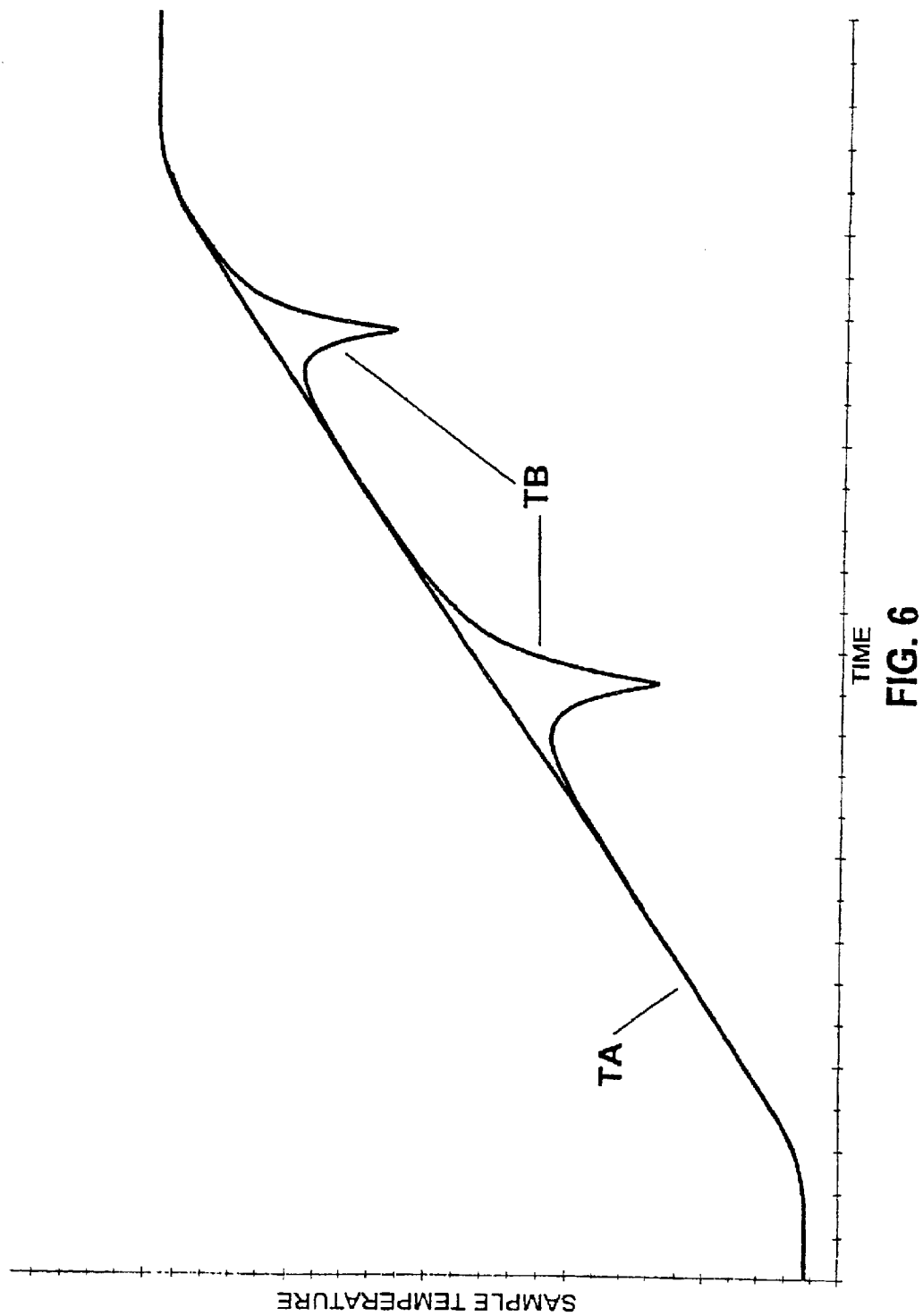
FIG. 6 is a plot of the temperature versus time of a single sample where the infrared thermography data was collected after the solids were contacted with a fluid that may be adsorbed by the solids in Example 4.

The plurality of solids would be cooled back to temperature T1 after having established a background or baseline profile for each solid in the array. A carrier gas containing at least one adsorbate would be contacted with the plurality of solids for a specified period of time, and then the array would be purged with an inert gas, both while the array would be at temperature T1. Heat would be transferred to the array while the array would be contacted with flowing inert gas. The temperature of each solid in the array would again be monitored using infrared thermography. Temperature (TB) versus time data would be sensed for each individual solid in the same manner as above resulting in data set 2 which is shown in FIG. 6. The array would be heated until the region mentioned above again reaches T2, with T2 being sufficiently high so that the adsorbate would desorb from the solids.

Figure 7:
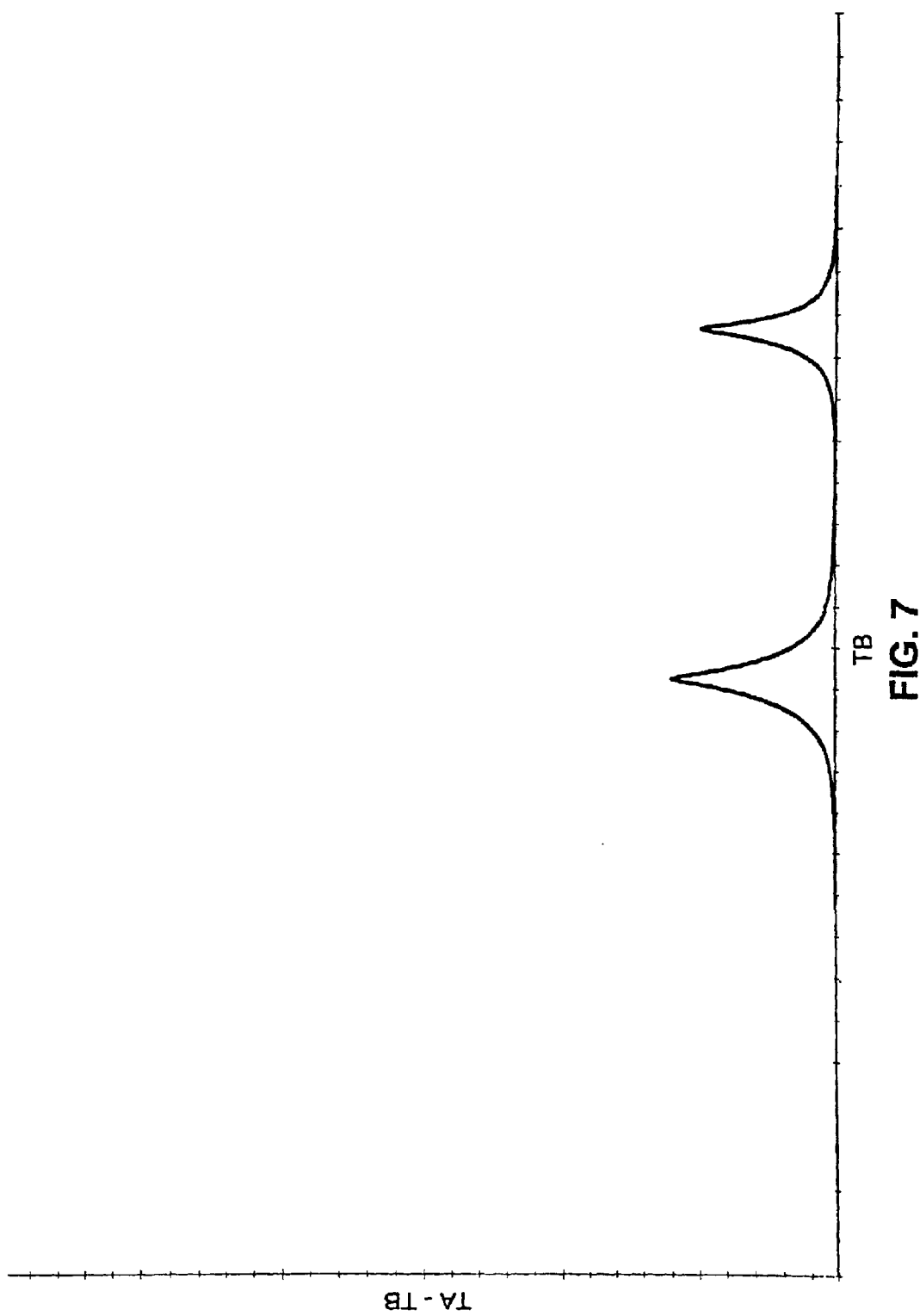
FIG. 7 represents the temperature data of FIG. 6 subtracted from the temperature data of FIG. 5 (which is a function of time) plotted against the temperature data of FIG. 6. Each peak of FIG. 7 represents a quantity of fluid desorbing at a specific temperature.

Data set 2 would be subtracted from data set 1 resulting in data set 3 (TA–TB) which would be a function of time "t". Time "t" of data set 3 would then be related to TB and TA–TB would be plotted versus TB, forming data set 4. The resultant data set 4, shown in FIG. 7, would be a series of peaks, each centered about a temperature TB for each solid contained in the assay. Each peak area would be functionally related to the quantity of adsorbate desorbing at that temperature in the same manner for each solid. Each peak centered on the same temperature TB in each data set 4 represents desorption from sites of substantially the same strength. Peak areas may be normalized to a sample contained in the assay or to a selected standard for relative comparisons among solids. Comparing the peak areas among samples would be indicative of, for example, the relative number of active sites, or reaction-promoting sites, contained in the samples tested as well as the strength of the active sites of the samples.

The peak areas may be modified by response factors if significant differences in the temperature-time profiles are found for each baseline. The response factors can be obtained by measuring the slope of a line fitted to the temperature rise occurring in the desorptive temperature region when the background (TA vs. time) data set is taken. The heat transfer rate to the assay should be such that the TA versus time data increases in linear fashion during the desorptive temperature region when the background (TA versus time) data set is taken.

EXAMPLE 5

An array of samples would be placed within a chamber that was constructed so that heat could be transferred to an individual solid location without affecting the temperatures of neighboring solids. Each location would have its own heating element receiving input from its own controller. The apparatus would be constructed to be able to individually flow fluid to contact individual solids in a similar and reproducible manner. The temperature of each location would be monitored by infrared thermography, and the temperature signal obtained by infrared thermography would be used as the temperature input for the heating element controllers.

Figure 8:
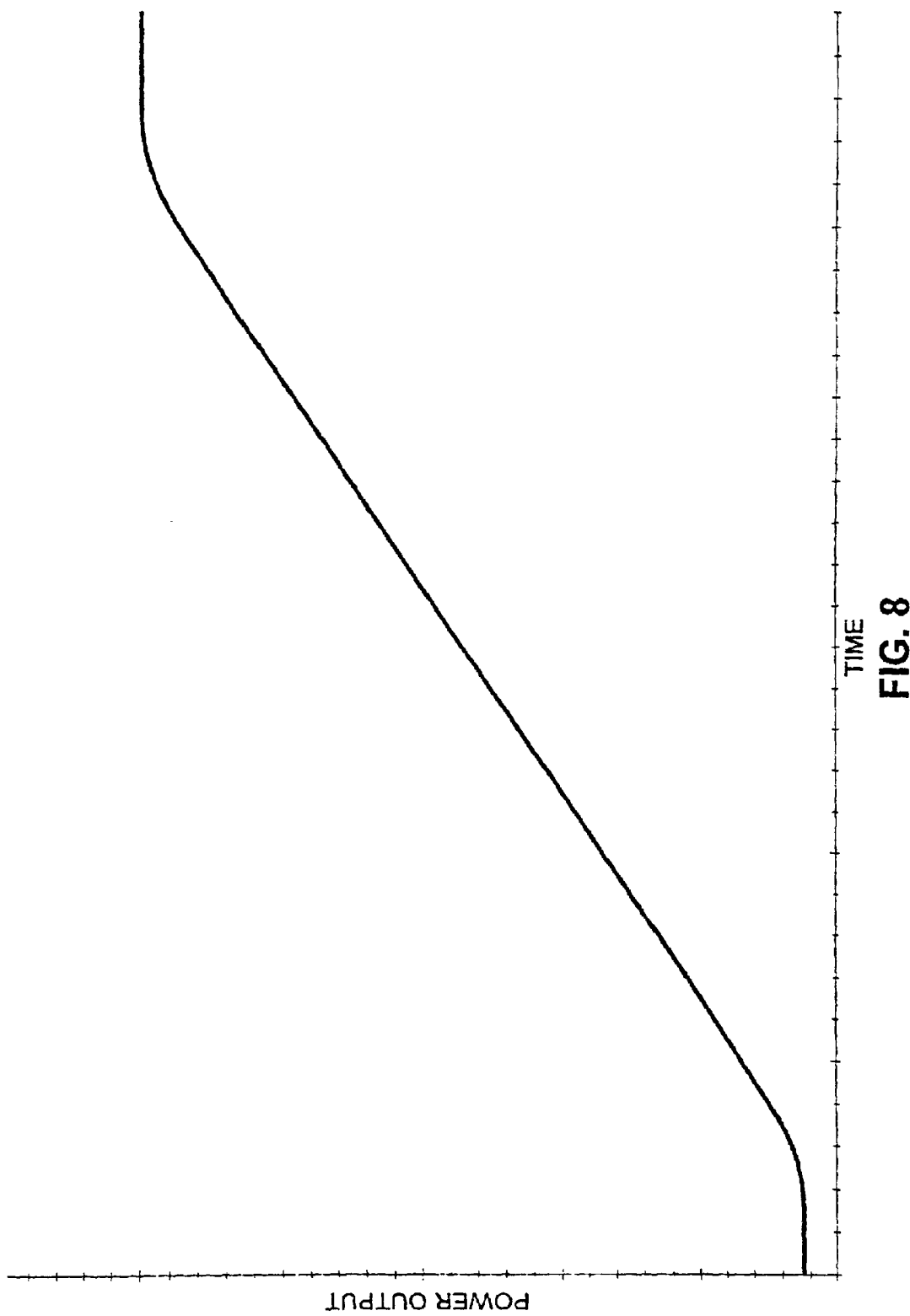
FIG. 8 is a plot of the temperature controller output data versus time of a single sample where the temperature controller output data was collected prior to the solids contacting a fluid that may be adsorbed by the solids in Example 5.

The entire array would be initially at temperature T1 and the same temperature ramp program, X° C./min., would be used in all temperature controllers. The temperature of all locations would be ramped according to this program while an inert gas would be passed through each solid until the array of solids reaches a temperature T2. Temperature (TA) versus time data would be sensed via infrared thermography for each individual solid or mixture of solids (data set 5) during the temperature ramp. It is expected that the temperature profiles would be the same for each location, showing only little variation. Temperature controller output power (PA) versus time would also be taken for each individual solid, called data set 6, see FIG. 8. Data set 6 be expected to show variations from cell to cell reflecting differences in heat transfer and heat capacity characteristics and heater properties.

The array of samples would then be cooled to temperature T1. A carrier gas containing an adsorbate would be introduced to each location individually, but under the same conditions. After sufficient equilibration time, and re-attainment of T1, the array would be purged with an inert fluid. While under inert fluid, the same temperature program would be run as above. The temperature of each individual solid or mixture of solids would again be monitored by infrared thermography. Temperature (TB) versus time data would be taken for each individual solid in the same manner as above. This temperature profile should match that found above for each sample and there should be only little variation between samples. Temperature controller power outputs (PB) versus time data would also be taken, resulting in data set 8, shown in FIG. 9. Sample to sample variations would be expected in the respective data sets 8. T2 would be sufficiently high to cause the adsorbate from each solid in the array to desorb.

Data set 6 would be subtracted from data set 8 resulting in data set 9. Data set 9 (PB–PA) would be a function of time, t, as shown in FIG. 10. The temperature at the time of the maximum of (PB–PA) using known relationships of time and TB would be calculated. Each peak area would be functionally related to the quantity of adsorbate that is desorbing at that temperature in the same manner for each sample. Peak areas could be normalized to a sample contained in the assay or to a standard so that the number of sites of a given strength could be relatively compared among the samples. Select samples could be tested in traditional calorimetric or temperature programmed desorption equipment to determine the actual adsorption energies associated with each temperature. This result could also be accomplished via the mathematical method disclosed above.

This embodiment relies on the measurement of the required power to achieve the substantially same temperature ramp at each sample location. Because power requirements normalized to a background for each cell would be used to generate the area data, the effect of differences in location heat transfer and heat capacity characteristics are minimized between sample locations. Heat transfer and heat capacity characteristics would be reflected in the differing heater power outputs (PA) required to generate data set 5, and their effect on the overall results would be removed when data set 6 is subtracted from data set 8. Alternatively, a controller power output program may be run to generate a temperature background. The same output program may be repeated to desorb the adsorbate. The variation in temperature profiles could be used to obtain the area data.

EXAMPLE 6

Figure 11:
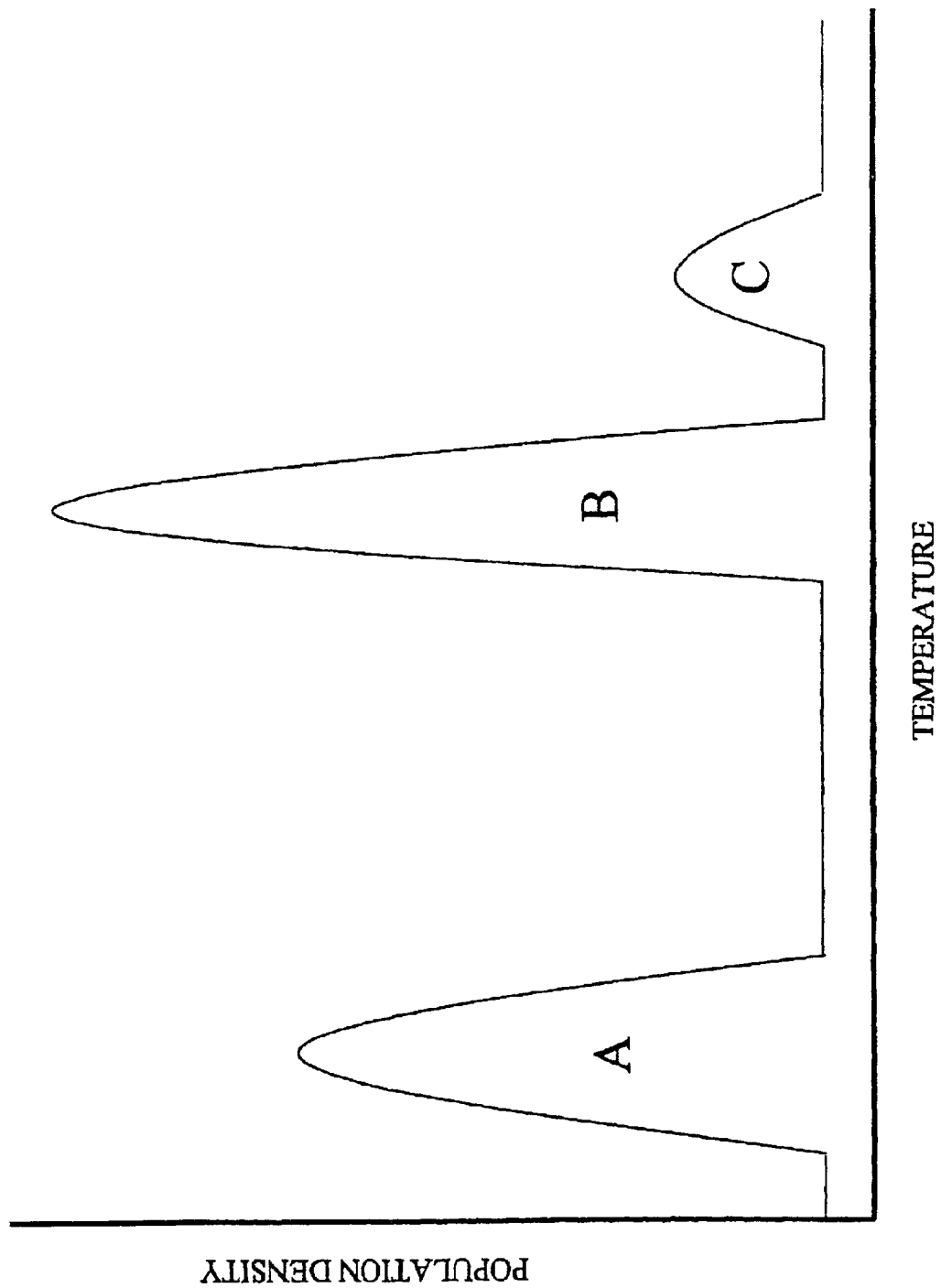
FIG. 11 is an example of a plot of a characteristic temperature distribution, temperature versus population density, as would be obtained in Example 6.

An array of solid samples would be placed in a chamber with an infrared transparent window. An infrared camera would be focused on the array of samples and a region of detector pixels centered on the samples would be defined. The chamber would be purged with an inert gas and a short burst of adsorbate containing gas would be directed at the array of samples. During contacting of adsorbate with the sample, infrared images would be collected, preferably at a fast rate. An image at a time or a selected image would constitute a thermogram of a sample. The data would be essentially a two-dimensional array of temperatures which can be reduced to a temperature distribution and a number of other characteristic parameters, such as shown in FIG. 11. The information in the thermogram may be further reduced by means of a parameter reflecting the spatial qualities of the temperature distribution. For example, the mean distance of all points within one standard deviation of the mean feature B from one another, or from the counterparts in feature C, could serve to further quantify the unreduced essentially visual data.

What is claimed is:

1. A method of quantifying the amount of adsorbate adsorbed on a solid comprising:
   a) contacting the solid with an adsorbate for a period of time;
   b) contacting the solid with an inert fluid while ramping the temperature of the solid at a specified ramp rate with a variable heat input profile with respect to a blank run;
   c) measuring the change in temperature of the solid during the contact with the inert fluid;
   d) recording the heat input profile during the contact with the inert fluid ($P_A$) and comparing to a blank run ($P_B$);
   e) determining a mathematical function, f(t), describing the deviation of the measured changes in temperature over time from the specified temperature ramp rate;
   f) determining a value of the desorption order, "m", that yields a linear relationship of $\ln[(-d\ N_A/dt)/N_A^m]$ vs $1/T$ where "$N_A$" is the total moles of adsorbate adsorbed on the solid, "t" is time, "$t_p$" is the time at which the extremum is observed, and "T" is temperature;
   g) determining the activation energy for desorption using:

$$-10^{13} \cdot \exp\left(\frac{-E_d}{RT_p}\right) + \frac{E_d}{RT_p^2}[\beta - f'(t)]/t_p \qquad (8)$$

when "m" is determined above to be 1, or using $$-v \cdot m \cdot N_A^{(m-1)} \cdot \exp\left(\frac{-E_d}{RT_p}\right) + \frac{E_d}{RT_p^2}[\beta - f'(t)]/t_p = 0 \qquad (7)$$

when "m" is determined above to be other than 1; and
   h) determining the quantity of adsorbate adsorbed on the solid using:

$$N_A = \int_{t_1}^{t_2} \frac{f(t)' \cdot C_{ps} + (P_B - P_A)}{\Delta H} dt \qquad (10)$$

where "$C_{ps}$" is the specific heat of the solid and $\Delta H$ is the heat of adsorption of adsorbate "A" which is substantially equal to the activation energy for desorption determined above.

2. The method of claim 1 wherein steps (a) through (h) are conducted on a plurality of solids.

3. The method of claim 1 wherein the expression describing the deviation of the measured changes in temperature over time from the specified temperature ramp rate, f(t)' is a polynomial described as:

$$f(t)' = \sum_{i=0}^{n} a_i \cdot t^i.$$

* * * * *